(12) United States Patent
Yang

(10) Patent No.: US 6,719,722 B1
(45) Date of Patent: Apr. 13, 2004

(54) SAFETY SYRINGE

(76) Inventor: Jih-Hsiung Yang, No. 822, Chungcheng Rd., Wufeng Hsiang, Taichung Hsien (TW)

( * ) Notice: Subject to any disclaimer, the term of this patent is extended or adjusted under 35 U.S.C. 154(b) by 0 days.

(21) Appl. No.: 10/411,243

(22) Filed: Apr. 11, 2003

(51) Int. Cl.[7] ................................................ A61M 5/00
(52) U.S. Cl. ...................................... 604/110; 604/195
(58) Field of Search ................................. 604/158, 218, 604/220, 128, 131, 181, 182, 194, 195, 110, 240–243, 196

(56) References Cited

U.S. PATENT DOCUMENTS 5,007,903 A * 4/1991 Ellard ......................... 604/195

* cited by examiner

Primary Examiner—Brian L. Casler
Assistant Examiner—K. C. Sirmons
(74) Attorney, Agent, or Firm—Troxell Law Office PLLC

(57) ABSTRACT

A safety syringe has a hollow barrel, a plug, a cord, a needle hub and a plunger. The hollow barrel has a distal open end, a proximal open end, a distal annular rib defined inside the proximal open end, a central annular rib defined inside the hollow barrel. The plug is detachably mounted inside the proximal open end of the hollow barrel. The needle hub is mounted in the plug. The plunger has a push rod and a seal mounted on the push rod and is received inside the hollow barrel. The cord connects to the plug and the seal. When using the safety syringe, the plunger pulls the cord connected to the plug, so the needle hub is pulled inside the hollow barrel to keep people from being hurt by an exposed needle.

1 Claim, 5 Drawing Sheets

SAFETY SYRINGE

BACKGROUND OF THE INVENTION

1. Field of the Invention

The present invention relates to a syringe, and more particularly to a safety syringe that can safely hold a used needle and prevent the syringe from being used more than once.

2. Description of Related Art

A conventional syringe has a hollow barrel, a plunger and a needle hub. The needle hubs of conventional syringes are easily inclined during use so the needle hubs are difficult to retract into the barrel. Due to contagious diseases, the needles of syringes and even the hollow barrels and plungers, should not be used again and should be discarded immediately after use. Also, to keep nurses, doctors or workers who deal with discarded syringes from getting injured or infected by used needles, a safety syringe is needed. The conventional safety syringe often has a complex structure, so to provide a simple and effective safe design for the needles of syringes is still needed.

To overcome the shortcomings with conventional syringes, the present invention provides safety syringes to mitigate or obviate the aforementioned problems.

SUMMARY OF THE INVENTION

The primary objective of the present invention is to provide a safety syringe that has a simpler structure than a conventional safety syringe and improves safety. The safety syringe in accordance with the present invention has a hollow barrel, a plug, a needle hub, a plunger and a cord. The hollow barrel has a distal open end, a proximal open end, a proximal annular rib, a central annular rib. The plug is detachably mounted inside the proximal open end of the hollow barrel. The needle hub is mounted to the plug. The plunger has a push rod and a seal mounted on the push rod and is slidably mounted inside the hollow barrel. The cord connects to the plug and the seal. When using the safety syringe, the plunger can pull the cord connected to the plug, so the needle hub can be pulled inside the hollow barrel to keep the used needle from injuring or infecting a person.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
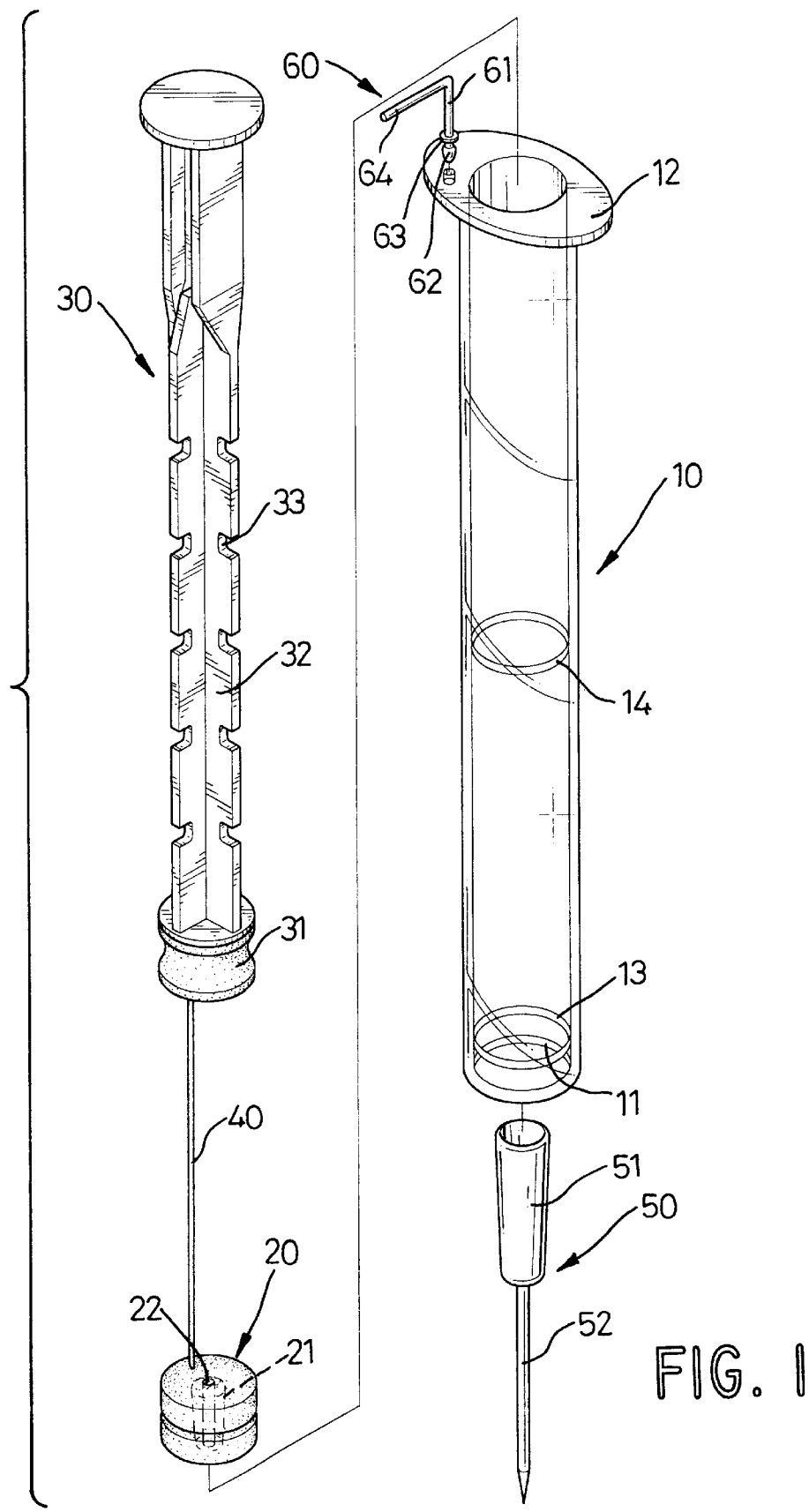
FIG. 1 is an exploded perspective view of the safety syringe in accordance with the present invention.
Figure 2:
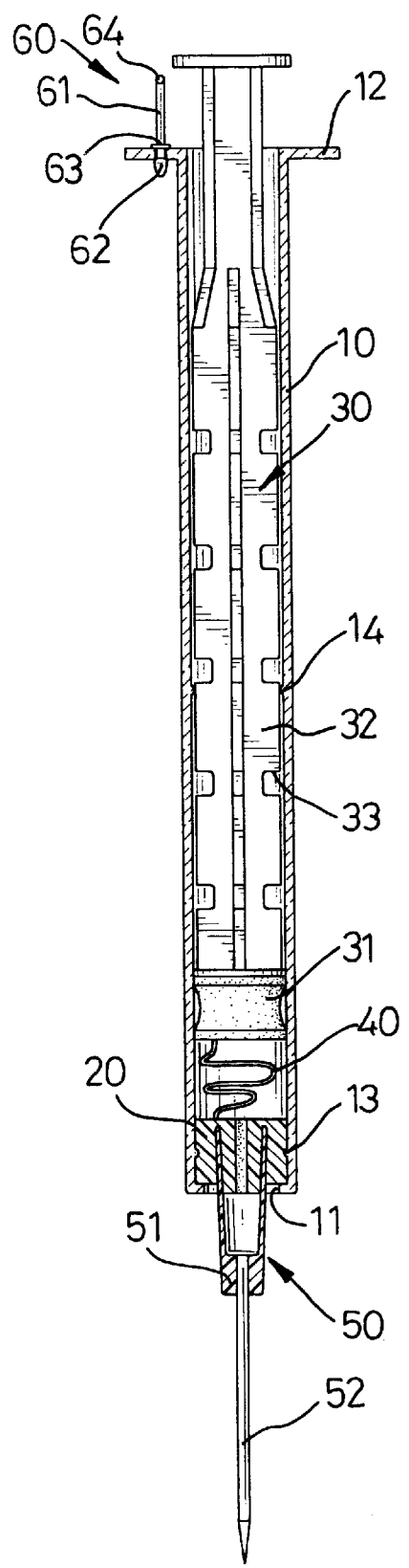
FIG. 2 is a side plan view of the safety syringe in FIG. 1.

With reference to FIGS. 1 and 2, a safety syringe in accordance with the present invention has a hollow barrel (10), a plug (20), a needle hub (50), a plunger (30), a cord (40) and a plunger lock (60).

The hollow barrel (10) is cylindrical and has distal open end (not numbered), a proximal open end (11), an inside surface (not numbered), an outside surface (not numbered), an annular flange (12), a lip (not numbered), a proximal annular rib (13) and an central annular rib (14). The annular flange (12) is defined radially around and extends out from the distal open end of the hollow barrel (10). The lip (not numbered) is defined radially around and extends radially inward from the proximal open end of the hollow barrel (10) so the proximal open end (11) is smaller than the distal open end. A proximal annular rib (13) is defined inside the hollow barrel (10) near the lip. The central annular rib (14) is defined inside the hollow barrel (10) equidistance between the open proximal end (11) and the open distal end.

The plug (20) is detachably engaged with the distal annular rib (13) inside the proximal open end (11) of the hollow barrel (10) and has a top surface (not numbered), a bottom surface (not numbered), a hub recess (21) and a needle hole (22). The hub recess (21) is defined through the plug (20) from the top surface to the bottom surface. The hub recess (21) is tapered. The needle hole (22) is defined through the plug (20).

The needle hub (50) is mounted in the plug (20) and has a connecting tube (51) and a needle (52). The connecting tube (51) is tapered and has a distal end (not numbered) and a proximal end (not numbered). The needle (52) is attached to the proximal end of the connecting tube (51) and has a central passage (not shown). The needle hub (50) is inserted through the top surface of the plug (20) and is mounted inside the hub recess (21).

The plunger (30) has a seal (31) and a push rod (32). The push rod (32) has a distal end (not numbered), a proximal end (not numbered) and a peripheral side (not numbered). The seal (31) has a top surface (not numbered) and a bottom surface (not numbered). The proximal end of the push rod (32) is attached to the top surface of the seal (31) and is mounted in the hollow barrel (10). The push rod (32) has multiple locking grooves (33) defined radially in the push rod (32).

The cord (40) has a top end (not numbered), a bottom end (not numbered) and a length. The top end of the cord (40) is attached to the bottom surface of the seal (31), and the bottom end of the cord (40) is attached to the bottom surface of the plug (20). The length of the of the cord (40) is equal to a distance between the top of the plug (20) and the bottom of the seal (31) when the plug (20) is engaged with the distal annular rib (13) and the bottom of seal (31) abuts the central annular rib (14). Furthermore, a distance between the proximal end (11) of the hollow barrel (10) and the central annular rib (14) is greater than a combined length of the needle hub (50) and the plug (20) so the needle (52) will be inside the hollow barrel (10) when the plug (20) engages the central annular rib (14).

The plunger lock (60) is L-shaped and has a longitudinal leg (61) and a transverse leg (64). The longitudinal leg (61) has a free end, a ball-prong (62) and a limit-ring (63). The ball-prong (62) is formed around the free end of the longitudinal leg. The limit-ring (63) is defined around the longitudinal leg (61) of the plunger lock (60) near the ball-prong (62). The ball-prong (62) is rotatably mounted in the annular flange (12).

Figure 3:
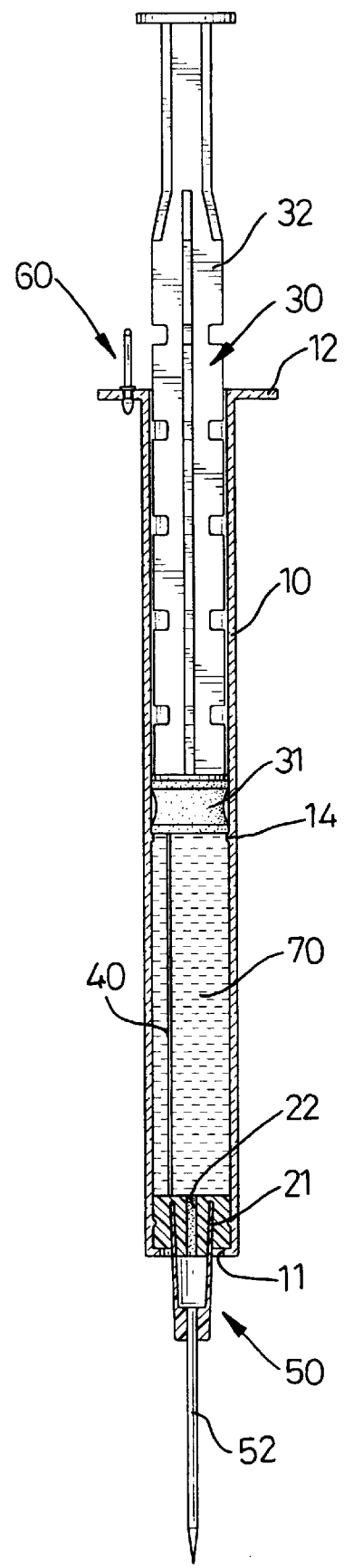
FIG. 3 is an operational side plan view of the safety syringe in FIG. 1.

With reference to FIGS. 2 and 3, the plunger (30) is pulled toward the distal end of the hollow barrel (10) after the needle (52) of the safety syringe is put into a patient's vein to take a blood sample (70). As the seal (31) and the cord (40) are pulled, the blood sample (70) is drawn into the hollow-barrel (10) between the seal (31) and the plug (20). When the seal (31) moves past the central annular rib (14), drawing the blood sample (70) is finished.

Figure 4:
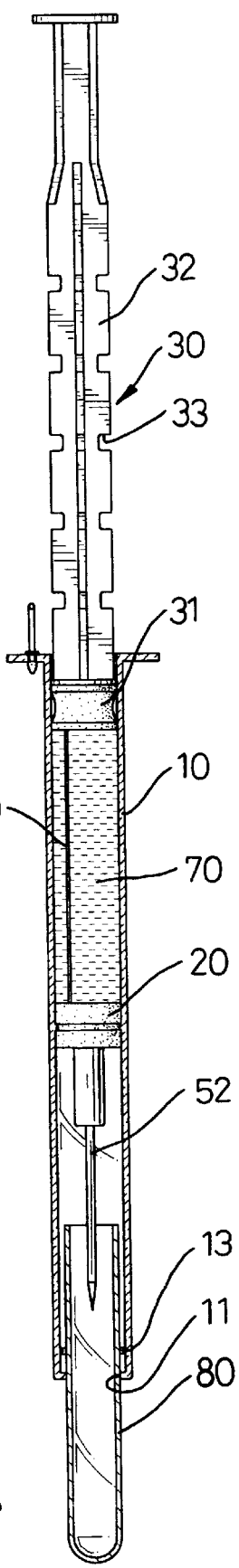
FIG. 4 is an operational plan view of the safety syringe in FIG. 1.
Figure 5:
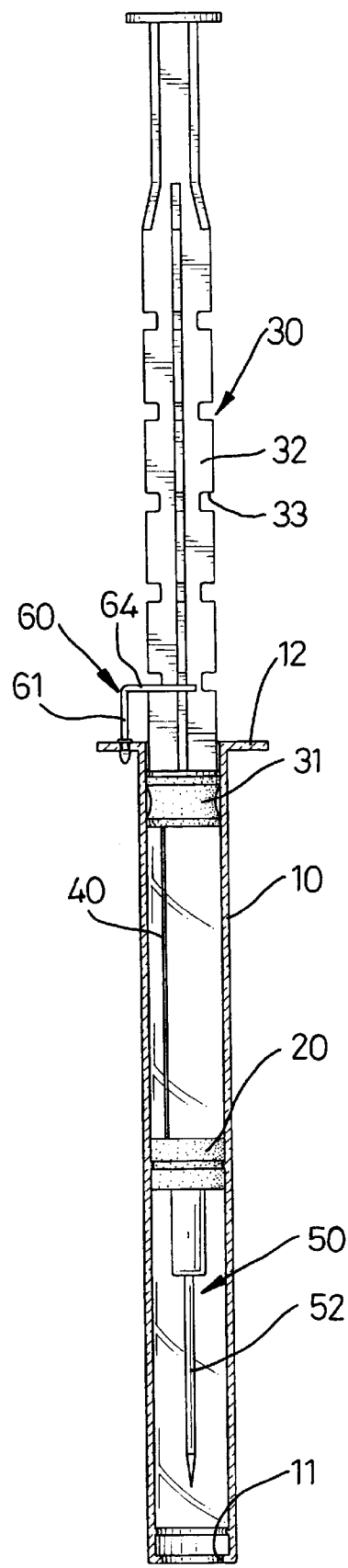
FIG. 5 is a side plan view of the safety syringe in FIG. 1 when the push rod is positioned.

With reference to FIGS. 4 and 5, the needle (52) is removed from the patient's vein, and the plunger (30) is pulled toward the distal open end of the hollow barrel (10). The moving plunger (30) pulls the cord (40) and disengages the plug (20) from the distal annular rib (13). The plunger (30) continues to pull the plug (20), the needle hub (50) and the blood sample (70) trapped between the seal (31) and the plug (20) until the plug (20) engages the central annular rib (14). A test tube (80) with an open end is used to collect the blood sample (70). When the needle (52) of the needle hub (50) is totally inside the hollow barrel (10), the open end of the test tube (80) is inserted into the hollow barrel (10) through the proximal end (11) to collect the blood sample (70). The blood sample (70) is injected into the test tube (80) by pressing the plunger (30). After the blood sample (70) has been injected into the test tube (80), the transverse leg (64) of the plunger lock (60) is pivoted into a corresponding locking groove (33) to ensure that the needle (52) is neither pulled nor pushed out of the hollow barrel (10). Then the test tube (80) is removed from the hollow barrel (10) and capped. The safety syringe can protect people from getting stabbed by the used needle (52) and prevents secondary use of the safety syringe.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising a hollow barrel, a plug, a needle hub, a plunger and a cord;

the hollow barrel being cylindrical and having
      a distal open end;
      a proximal open end;
      an inside surface;
      an outside surface;
      an annular flange formed radially around extending out from the distal open end;
      a lip formed radially around and extending inward from the proximal open end of the hollow barrel;
      a proximal annular rib defined inside the hollow barrel near the lip and
      a central annular rib defined inside the hollow barrel;
   the plug detachably engaged with the proximal annular rib inside the proximal open end of the hollow barrel and having
      a top surface;
      a bottom surface;
      a hub recess being tapered and defined through the plug from the top surface to the bottom surface; and
      a needle hole defined through the plug; the needle hub mounted in the plug and having
      a connecting tube being tapered and having a distal end and a proximal end; and
      a needle attached to the proximal end of the connecting tube and having a central passage;
   the plunger having
      a push rod being mounted inside the hollow barrel and having
         a proximal end; and
         a seal having
            a top surface attached to the proximal end of the push rod; and
            a bottom surface; and
   the cord connected between the plug and the plunger and having
      a top end attached to the bottom surface of the seal; and
      a bottom end attached to the top surface of the plug;
   wherein a distance between the proximal end of the hollow barrel and the central annular rib is greater than a combined length of the needle hub and the plug.

* * * * *